United States Patent [19]

Hirschowitz et al.

[11] 4,328,809
[45] May 11, 1982

[54] DEVICE AND METHOD FOR DETECTING THE POTENTIAL LEVEL OF THE ELECTROMAGNETIC FIELD OF A LIVING ORGANISM

[75] Inventors: Barry H. Hirschowitz, Box Nine, Brooklandville, Md. 21022; Kwok-Leung Li, Towson, Md.

[73] Assignee: Barry Herbert Hirschowitz, Brooklandville, Md.

[21] Appl. No.: 52,258

[22] Filed: Jun. 26, 1979

Related U.S. Application Data

[63] Continuation-in-part of Ser. No. 726,197, Sep. 24, 1976, abandoned.

[51] Int. Cl.³ ............................................. A61B 5/00
[52] U.S. Cl. ................................................... 128/653
[58] Field of Search ............... 128/639, 640, 653, 693, 128/695, 696, 709, 710, 711, 734, 735, 738, 635

[56] References Cited

U.S. PATENT DOCUMENTS

| | | | |
|---|---|---|---|
| 3,052,232 | 9/1962 | Zworykin et al. | 128/731 |
| 3,323,515 | 6/1967 | Foner et al. | 128/710 |
| 3,327,117 | 6/1967 | Kamentsky | 128/653 |
| 3,528,405 | 9/1970 | Schuler | 128/630 |
| 3,555,529 | 1/1971 | Brown et al. | 128/653 |
| 3,568,662 | 3/1971 | Everett et al. | 128/639 |
| 3,717,141 | 2/1973 | Krohn et al. | 128/711 |
| 3,749,089 | 7/1973 | Derr | 128/738 |
| 3,841,309 | 10/1974 | Salter et al. | 128/731 |
| 3,874,368 | 4/1975 | Asrican | 128/734 |
| 3,920,003 | 11/1975 | Ash et al. | 128/738 |
| 3,924,609 | 12/1975 | Friedenberg et al. | 128/738 |
| 3,949,736 | 4/1976 | Vrana et al. | 128/734 |
| 3,971,366 | 7/1976 | Motoyama | 128/639 |
| 4,182,314 | 1/1980 | Boughton | 128/734 |
| 4,216,462 | 8/1980 | McGrath et al. | 128/710 |

FOREIGN PATENT DOCUMENTS

2727396 12/1978 Fed. Rep. of Germany ...... 128/640

OTHER PUBLICATIONS

Burr et al., "Yale Journal of Biology & Medicine" vol. 9, 1936 pp. 65-76.
Ravitz, "N.Y. Academy Science Annals," vol. 98, 1962, pp. 1144-1201.
Langman et al, "American Journal of Obstetrics & Gynecology", vol. 43, 1942 pp. 223-230.
Burr et al., "Yale Journal of Biology & Medicine" vol. 17, 1945 pp. 465-478.
Burr et al., "Yale Journal of Biology & Medicine" vol. 21, 1949 pp. 249-253.
Takamura et al., "Toshiba Review" No. 48, May-Jun. 1970 pp. 11-16.
Geddes et al., "American Journal of Medical Electronics" Jan.-Mar. 1964 pp. 16-27.

*Primary Examiner*—William E. Kamm
*Attorney, Agent, or Firm*—Saidman & Sterne

[57] ABSTRACT

A device and method for detecting the potential level of the electromagnetic field present between a reference point and a test point of a living organism is disclosed. A reference electrode provides a first signal indicative of the potential level of the electromagnetic field at the reference point. A test electrode provides a second signal indicative of the potential level of the electromagnetic field at the test point. More than one test electrode and corresponding second signals can be employed. An analog-to-digital converter responsive to the first and second signals generates a digital signal as a function of the potential difference between the first and second signals. A processor provides an output signal indicative of a parameter or parameters of the living organism as a function of the digital signal. In addition, a low pass filter can be provided ahead of the analog-to-digital converter for filtering out undesired charges and alternating current signals from the first and second signals. The analog-to-digital converter can sample the potential difference between the first and second signals at a desired rate, and the processor can generate the output signal as a function of the digital signal and a stored program. The output signal can provide a diagnostic and predictive function, for example, of the presence or absence of atypical cellular growth, ovarian events, cancer, neurological activity, vitality of seeds, etc.

39 Claims, 6 Drawing Figures

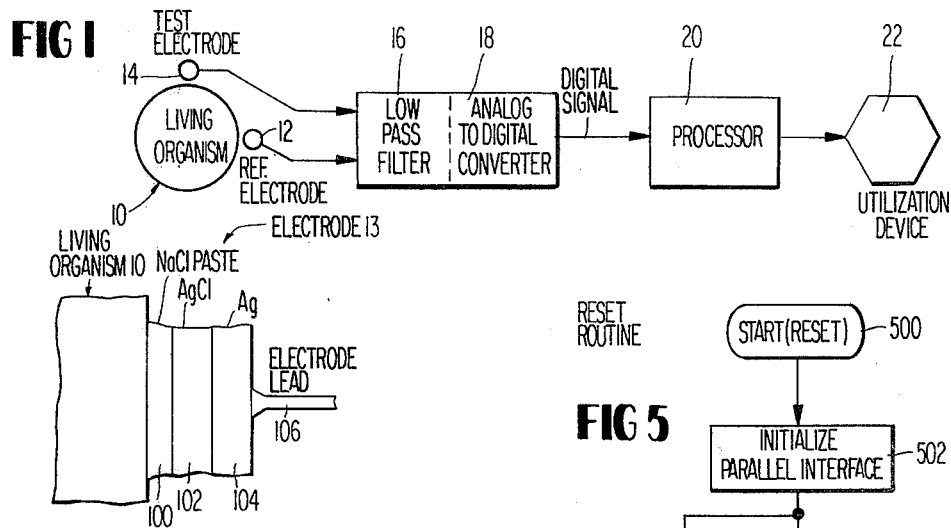
FIG 1
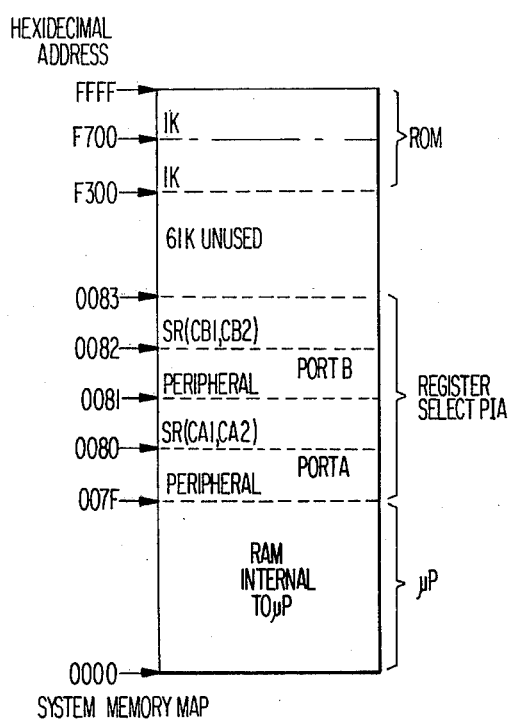
FIG 2
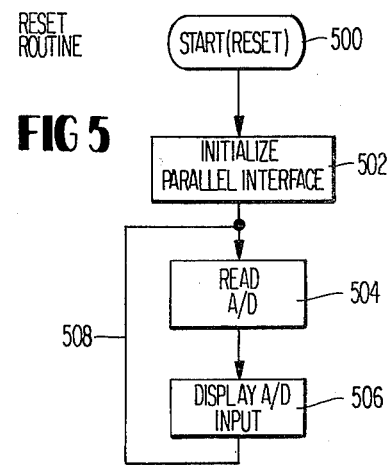
FIG 5
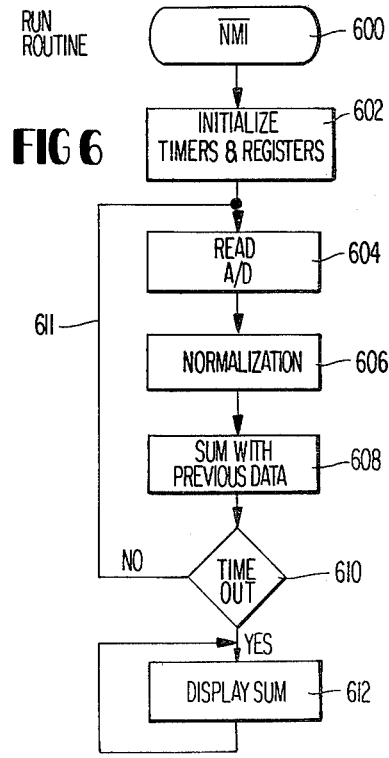
FIG 6
FIG 4

DEVICE AND METHOD FOR DETECTING THE POTENTIAL LEVEL OF THE ELECTROMAGNETIC FIELD OF A LIVING ORGANISM

CROSS-REFERENCE TO RELATED APPLICATION

This application is a continuation-in-part of Application Ser. No. 726,197, filed Sept. 24, 1976, now abandoned.

BACKGROUND OF THE INVENTION

1. Field of the Invention

The present invention relates generally to apparatus and methods for detecting parameters of living organisms and, more particularly, relates to a device and method for providing an output signal indicative of a parameter or parameters of a living organism, which output signal being derived by detecting the potential of the electromagnetic field present between a reference point and a test point or test points of a living organism.

2. Prior Art

Over the years there have been two prevailing theories on the operation of living organisms. The more widely accepted theory even to this day is that all living organisms are made up of discontinuous entities called cells, which are organized in accordance with the interaction between themselves. This is often referred to as the cell theory of life or physiology. Its modern origin is based on the work, among others, of Harvey and Laviosier, who respectively applied this atomistic theory to explain the circulation of blood and the chemical nature of respiration and metabolism. Their analysis of life was based upon the mechanistic premise that life was no more than a complex reaction between discontinuous chemical or atomic entities. In summary, this analysis states that a living organism is equal to the sum of its parts. Even today, molecular biology and medicine rests on this analysis.

The less widely accepted theory is often referred to as vitalism. Vitalism states that a living organism is greater than the sum of its atomic constituents. Vitalism in essence postulates that there is a non-atomic force that acts to organize the atomic constituents. This non-atomic force was used to explain the constancy of form of organisms over time despite ongoing chemical reactions, which constancy could not be explained by the cell theory. Vitalism has gone under several names: Driesch's "entelechy," Rignano's "biological energy," Child's "physiological gradient," and Kohler's "Gestalten." Vitalism, however, fell into disrepute because the non-atomic force could not be empirically demonstrated.

In the 1920's and 1930's, Harold S. Burr of the Yale School of Medicine and Filmer S. C. Northrop of the Yale School of Law set forth their theory addressing the problems of both mechanism and vitalism. Their electrodynamic theory states that "the pattern or organization of any biological system is established by a complex electrodynamic field, which is in part determined by its atomic physio-chemical components and which in part determines the behavior and orientation of those components." Burr, H. S. and F. S. C. Northrop, "The Electro-Dynamic Theory of Life," *Quarterly Revue of Biology*, Vol. 10, pages 322-333, 1935. The theory synthesized the cell and vitalism theories by applying modern relativistic field physics to biological systems. In essence, this electromagnetic field (also referred to as a quasi-electrostatic field) is the intermediary vector force between Cartesian and Gaussian coordinates.

This electro-dynamic field postulated by the theory was empirically demonstrated. Burr, H. S. and C. I. Hovland, "Bio-Electric Potential Gradients in the Chick," *Yale J. Biology and Medicine*, Vol. 9, pages 247-158, 1937. Burr, H. S. and C. I. Hovland, "Bio-Electric Correlates of Development in Amblystoma," *Yale J. Biology and Medicine*, Vol. 9, pages 540-549, 1937. The potential level of the electro-dynamic field was measured using a very high impedance vacuum tube volt meter (VTVM) and special electrodes. Each electrode was designed in accordance with Willard Gibb's equations governing the mechanics of fluid junction potentials so as not to generate an offset potential between itself and the organism being measured. The high impedance, typically 10 megohms, of the VTVM was calculated in accordance with Maxwell's equations and was necessary to prevent any appreciable current from being drawn from the organism and to eliminate any errors caused by changes in the resistance of the organism test interface. The electro-dynamic field would be distorted causing a disturbance to the organism and an error in the potential level value if appreciable current was drawn during the test.

Despite repeated empiric demonstrations of the validity of the electro-dynamic field theory by Dr. Burr and others, major technical problems contribute substantially to its failure to become an established diagnostic and predictive means for indicating the state of a parameter or parameters of a living organism. Reference and test electrodes produce errors due to their design, temperature variations, and the uneven pressure between the organism and the electrodes. The available structures and configurations of these electrodes is also quite limited and cannot be tailored for many test applications.

The potential level of the electromagnetic field of organisms usually does not exceed an absolute value of 100 millivolts. Therefore, a resolution of 100 microvolts is needed to obtain a measure of the field of sufficient accuracy to ascertain a diagnostic parameter or parameters. Conventional high gain instrument operational amplifiers exhibit a characteristic temperature coefficient for output bias voltage of 700 microvolts per degree Centigrade. Thus, the desired resolution of 100 microvolts cannot be achieved unless the ambient temperature of the operational amplifier is kept within one-seventh degree Centigrade during the entire test. This narrow temperature tolerance is not possible, however, unless a very expensive, technically complicated, physically cumbersome, and high electrical load temperature control system, such as a temperature oven, is used in conjunction with the operational amplifier.

Another problem associated with temperature variation is that the very slowly varying electromagnetic field often has a period of substantial time, such as 30 seconds or more. If real time integration is used as the measuring technique, conventional high gain operational amplifiers cannot provide the necessary 100 microvolt resolution for a time period greater than 2 seconds, because the ambient temperature of the amplifier cannot be maintained within the one-seventh degree centigrade range without the use of a temperature control system as stated above.

A further problem is the presence of undesired alternating current signals having frequencies, for example, greater than 100 Hertz and undesired charges present on the electromagnetic field signals furnished to the measuring apparatus and method by the reference and test electrodes. These undesired alternating current signals and charges act to mask the desired slowly varying DC signal indicating the potential of the electromagnetic field. The problem becomes particularly severe in areas having high levels of electromagnetic radiation produced by television, radio, communication radio frequency transmissions, etc., which affect the electromagnetic fields of organisms. In addition, natural environmental events, such as sunspots, also affect the electromagnetic field of organisms.

OBJECTS OF THE INVENTION

It is an object of the present invention to provide a device and method of measuring the potential level of the electromagnetic field present between a reference point and a test point or test points of a living organism.

It is another object of the present invention to provide a device and method for providing an output signal indicative of a parameter or parameters of a living organism in accordance with the potential level of the electromagnetic field present between a reference point and a test point or test points.

It is a further object of the device and method of the present invention to provide reference and test electrodes used in measuring the potential level of the electromagnetic field, which electrodes do not create a substantial battery effect between themselves and the living organism and which can be fabricated to assume various configurations and structures suitable for tests down to the unicellar level.

It is another object of the method and device of the present invention to provide a resolution of at least 100 microvolts in the measurement of the potential level of the electromagnetic field without the use of temperature control systems, such as a temperature-controlled oven.

It is a further object of the device and method of the present invention to provide accurate measurement of the potential level of the electromagnetic field having a time period greater than 2 seconds.

It is another object of the device and method of the present invention to eliminate substantially undesired charges and alternating current signals from the slowly varying DC signal indicating the potential level of the electromagnetic field.

It is a further object of the device and method of the present invention to produce a diagnostic and predictive function, for example, of the presence or absence of atypical cellular growth, ovarian events, cancer, neurological activity, etc., in accordance with the potential level of the electromagnetic field of the organism.

It is an additional object of the device and method of the present invention to provide a diagnostic and/or predictive device of low cost, small size and weight, and low power consumption, while still providing high accuracy and reliability as well as requiring only a low level of skill to operate.

These and other objects are achieved by the method and device of the present invention.

SUMMARY OF THE INVENTION

A device and method for detecting the potential level of the electromagnetic field present between a reference point and a test point of a living organism is disclosed. A reference electrode provides a first signal indicative of the potential level of the electromagnetic field at the reference point. A test electrode provides a second signal indicative of the potential level of the electromagnetic field at the test point. More than one test electrode and corresponding second signals can be employed. An analog-to-digital converter responsive to the first and second signals generates a digital signal as a function of the potential difference between the first and second signals. A processor provides an output signal indicative of a parameter or parameters of the living organism as a function of the digital signal. In addition, a low pass filter can be provided ahead of the analog-to-digital converter for filtering out undesired charges and alternating current signals from the first and second signals. The analog-to-digital converter can sample the potential difference between the first and second signals at a desired rate, and the processor can generate the output signal as a function of the digital signal and a stored program. The output signal can provide a diagnostic and predictive function, for example, of the presence or absence of atypical cellular growth, ovarian events, cancer, neurological activity, etc.

A preferrable form for the reference and test electrodes is that which does not create a substantial battery effect between itself and the point of the organism under test. One preferred form for the electrode comprises concentrated NaCl disposed on said reference or test point of the living organism. An AgCl electrode is disposed on the surface of the NaCl opposite the reference or test point. An Ag electrode is electrically connected to the AgCl electrode and provides the first or second signal respectively. Alternately, a NaCl polymer or colloid can be employed, allowing the structure and configuration of the electrode to take any shape needed for a particular test application.

The effective input impedance of the analog-to-digital converter can be in the range of 5 megohms to 1,000 megohms, with the typical value being 10 megohms. The 3 dB cutoff frequency of the low pass filter can be greater than or equal to 100 Hertz.

In one preferred form, the processor comprises a central processor for sending and receiving digital data to or from a data bus in accordance with a read or write signal, respectively, and address and control signals. An interface responsive to said digital signal provides the digital signal to the data bus in accordance with said read signal and selected address and control signals, and provides the output signal from the data bus in accordance with the write signal and selected address and control signals. A stored program means provides program instructions to said data bus in accordance with selected address and control signals. Preferably the central processor is a microprocessor and the stored program means is a read only memory.

The present invention may further comprise a utilization means for providing a function in response to said output signal. One suitable form for the utilization means is a visual display. Another suitable form is a telemetry system and a further suitable form is a storage device.

The method of the present invention detects the potential level of the electromagnetic field present between a reference point and a test point of a living organism in accordance with the following steps. A first signal is provided indicative of the potential of the electromagnetic field at the reference point. A second signal is provided indicative of the potential of the electromagnetic field at the test point. (More than one second signal can be provided.) A digital signal is generated as a function of the potential difference between the first and second signals. An output signal is provided indicative of a parameter or parameters of the living organism as a function of the digital signal.

The output signal can provide a diagnostic and predictive function, for example, of the presence or absence of atypical cellular growth, ovarian events, cancer, neurological activity, etc. In addition, the first and second signals can be low pass filtered before their difference is converted to a digital form. The first and second signals can be sampled to produce a digital signal for each sample. Furthermore, the output signal can be any statistical function of any set of digital signals including an average or mean of the digital signals. The step of providing a first signal can utilize a first electrode which does not create a substantial battery effect between itself and the reference point, and the step of providing a second signal can utilize a second electrode which does not create a substantial battery effect between itself and the test point.

BRIEF DESCRIPTION OF THE DRAWINGS

FIG. 1 is a block diagram of the device and method of the present invention for measuring the potential level of the electromagnetic field present between a reference point and a test point or test points of a living organism.

FIG. 2 is a side block diagram representation of the elements of a preferred electrode used at either the reference point or the test point of the living organism.

FIG. 4 is a system memory map of the embodiment of FIG. 3.

FIG. 5 is a flow chart of the reset routine of the embodiment of the present invention of FIG. 3.

FIG. 6 is a flow chart of the run routine of the embodiment of the present invention of FIG. 3.

DETAILED DESCRIPTION OF THE INVENTION

Figure 3:
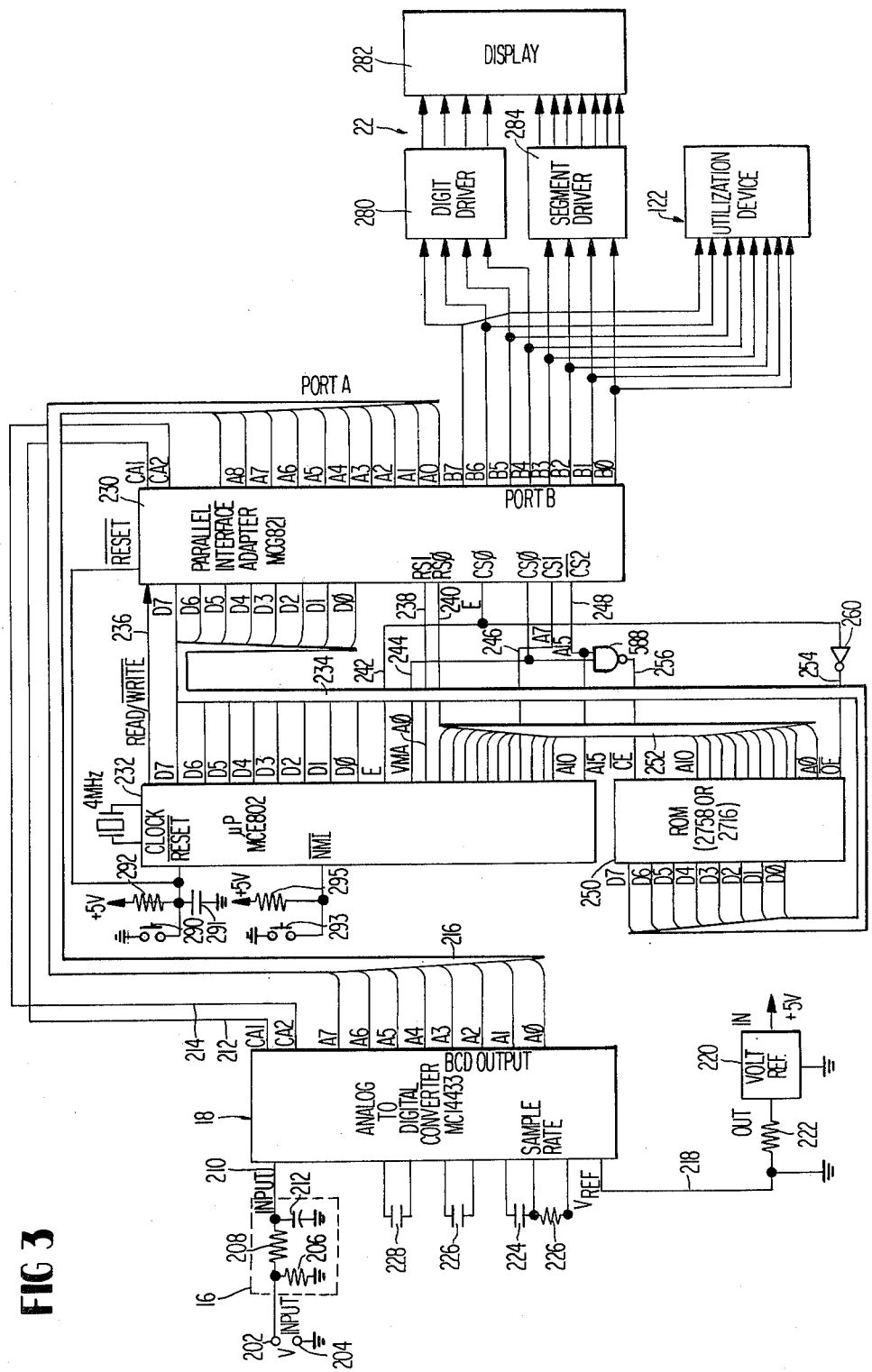
FIG. 3 is a schematic diagram of a preferred embodiment of the device for implementing the method of the present invention.

Referring now to FIG. 1, a block diagram of the basic embodiment of the device and method of the present invention for measuring the potential level of the electromagnetic field present between a reference point and a test point or points of a living organism is shown.

The living organism, designated generally by reference numeral 10, generates an electromagnetic field of either a positive or negative polarity and having a potential level in the millivolt range. Most living organisms do not have an electromagnetic field having a potential level greater than 100 millivolts. It should be understood that the term potential and potential level hereinafter refers both to the absolute value and to the polarity of the electromagnetic field. Depending upon the parameter or parameters being tested, one reference point and one or more test points on the surface of the living organism 10 are used to measure the electromagnetic field of the living organism. For purposes of explanation, only one test point is shown. It should be understood, however, that the present invention encompasses the use of one or more test electrodes as well as one or more reference electrodes.

A reference electrode 12 is disposed on the living organism at a reference point, and a test electrode 14 is disposed on the living organism at a test point. The reference electrode 12 and the test electrode 14 can take any suitable form. The device and method of the present invention measures the electromagnetic field 14 inherent in the living organism 10 between the reference electrode 12 and the test electrode 14.

The signal (first signal) provided by the reference electrode 12 is supplied to an input of a low pass filter, designated generally by reference numeral 16. Similarly, the signal (second signal) provided by the test electrode 14 is applied to another input of the low pass filter 16. Low pass filter 16 acts to remove undesired high frequency signal components superimposed on the signals from reference electrode 12 and test electrode 14. As stated above, the electromagnetic field is a slowly varying DC voltage signal. Undesired AC components appear on this signal due to static charges, electromagnetic interference, and signals from other sources.

The output from low pass filter 16 is applied to the input of an analog-to-digital converter, designated generally by reference numeral 18. Analog-to-digital converter 18 preferably has a high input impedance, for example, greater than 8 megohms, so as not to cause any appreciable current to be drawn from the organism during the test of the electromagnetic field potential level. Analog-to-digital converter 18 can be of any suitable form for providing a digital signal output indicative of the potential level of the differential analog signal at its input.

The digital signal output from analog-to-digital converter 18 (which is representative of the potential level of the analog signals at its input provided by low pass filter 16) is provided to the input of a processor, designated generally by reference numeral 20. Processor 20 performs designated functions on the digital signal provided by analog-to-digital converter 18, so as to provide an output signal indicative of a parameter or parameters of the living organism 10 whose electromagnetic field is being sensed. Processor 20 can take any number of suitable forms. Processor 20 can, for example, sum the normalized values of the digital signals so as to provide an average or mean signal at its output. Similarly, processor 20 can note the change of sign of the digital signals so as to indicate a desired parameter or parameters of the living organism. It should also be noted that processor 20 can provide an output signal indicative of more than one parameter of the living organism from a single series of tests of the potential level of the electromagnetic field. Furthermore, processor 20 can provide an output signal indicative of any function involving the interrelationship of two or more parameters of the same organisms over time.

In some of the applications of the device and method of the present invention, one or more of the digital signals are analyzed by processor 20 to provide the output signal indicative of the parameter of the living organism under test. It has been found, for example, when the period of the electromagnetic field is long, for example, 30 seconds, a digital sample of the analog signal should be taken once every sixth of a second. Under this test routine, 180 samples of the electromagnetic field are taken within the course of a 30 second test period, which corresponds roughly to the period of the electromagnetic field. These 180 digital data are normalized and summed to provide an average or mean value of the electromagnetic field over the 30 second test period. This average signal constitutes the output signal indicative of the parameter of the living organism under test. The sign of the output signal can also be indicative of the parameter or parameters.

Processor 20 can take any suitable mechanization, for example, a program controlled microprocessor system, as described below. In addition, processor 20 could take the form of a hard-wire system without a program control. All that is required is one or more digital signals be used as samples to provide the output signal indicative of the parameter or parameters of the living organism.

The output signal from processor 20 is provided to a utilization device, designated generally by reference numeral 22. Utilization device 22 can take any number of suitable forms. For example, utilization device 22 could be in the form of a visual display, typically disposed on the front of the test instrument. The visual display could either be a numerical display of the potential level and/or polarity of the electromagnetic field over the course of the test period, or could be a light or sound that either indicates the presence or absence of the parameter or parameters being measured. In addition, utilization device 22 could take the form of a storage device for storing the output signal or signals, so that output signals over successive tests could be retained for future analysis. Furthermore, utilization device 22 could take the form of a telemetry unit for transmitting the output signal to a receiving station. Other forms of the utilization device 22 are contemplated by this invention.

Reference electrode 12 and test electrode 14 can take any suitable form. However, neither of these electrodes should cause a substantial battery effect between itself and the point of the living organism under test. One suitable form for either electrode 12 or electrode 14 which does not produce a substantial battery effect is that which utilizes a concentrated NaCl material 100 disposed between the living organism 10 and the surface of a layer 102, substantially silver chloride (AgCl), of the electrode 13, as shown in FIG. 2. Electrically attached to the silver chloride layer 102 is another layer 104, substantially made up of silver (Ag). The electrode lead 106, in turn, is electrically attached to the silver electrode 104. This configuration for the electrode 13 prevents any substantial battery effect from being created between the living organism 10 and electrode 13. In addition, an insulated housing (not shown) can be provided around electrode 13 to reduce undesired electromagnetic interference and to guard against leakage.

The NaCl material 100 can be obtained from several commercial sources, including Beckman Instruments, Inc., of the United States. In addition, PolySciences, Inc., of the United States produces a NaCl polymer material which also performs the same function as the NaCl material. The NaCl polymer or colloid material is particularly advantageous because it allows an electrode 13 of any desired shape or configuration to be fabricated. Thus, for example, measurements down to the molecular level can be achieved using micro-pipette type electrodes. It should be noted that other forms for material 100 are contemplated by the present invention.

A preferred embodiment of the device for implementing the method of detecting the potential level of the electromagnetic field present between a reference point and a test point or points of a living organism of the present invention is shown in FIG. 3. The system shown in FIG. 3 is a microprocessor based system whose processor 20 can provide, for example, a statistical function of the digital signals provided by the analog-to-digital converter 18. Like numbers between FIGS. 1 and 3 refer to the same basic functional components between the block diagram system of FIG. 1 and the actual embodiment of FIG. 3.

Referring now to FIG. 3, an input 202 is connected to test electrode 14 (not shown). Similarly, an input 204 is connected to the reference electrode 12 (not shown). Input 204 is also connected to electrical ground.

Input 202 is connected to the input of the low pass filter contained within dashed-line box 16. Low pass filter 16 is made up of a resistor 206 connected between input 202 and electrical ground. A resistor 208 is connected between input 202 and the input 210 of the analog-to-digital converter 18. A capacitor 212 is connected between input 210 and electrical ground.

The input impedance of analog-to-digital converter 18 is of a very high value, for example, 1,000 megohm range, because the input active devices of analog-to-digital converter 18 are MOSFET's. Consequently, resistor 208 is used to shunt this value to the 10 megohm range. In this case, the resistance value for resistor 206 is approximately 10 megohms. Resistor 206 thus functions as setting the input impedance of analog-to-digital converter 18.

Resistor 208 acts as a current limiter so that the analog-to-digital converter 18 is prevented from being burned out in the event that input 204 is connected to a high voltage source accidentally. Resistor 208 also prevents charge build-up from occurring on the input active devices of analog-to-digital converter 18 which could result in their being damaged substantially. Because of the very high input impedance exhibited by the input active devices of analog-to-digital converter 18, charges tend to build-up on these devices which can cause electrical failure. Resistor 208 also prevents this.

Capacitor 216 and resistor 208 also function as a low pass filter. The 3 dB frequency cutoff point of this RC combination is set so as to pass signals having a frequency below a preselected point. For example, the preselected frequency point can be 100 Hertz.

Analog-to-digital converter 18 provides a binary-coded-decimal (BCD) output on lines A0 through A7 as a digital signal representation of the analog signal present at its input 210. Analog-to-digital converter 18 can be of any suitable type. One presently available version for analog-to-digital converter 18 is that designated as the MC14433 made by the Motorola Corporation of the United States.

The CA1 line from analog-to-digital converter 18 is an end of conversion signal indicating that the sample present on the BCD output lines is indeed a proper digital signal representation of the analog signal present at the input 210. In the case of the MC14433, the EOC signal present on line CA1 occurs on the rising edge of the pulse. The analog-to-digital converter MC14433 is of the dual slope conversion type. That is to say, a set time period is used to cause the analog signal present at the input 210 to charge a known capacitor. Thereafter, a known current source is used as a means for discharging this known capacitor. The time that it takes to discharge the signal present on the known capacitor indicates the digital level of the analog signal present at input 210. In the event that the capacitor cannot be discharged by the known current source within the time period, an over-range (OR) signal is provided on line CA2. This over-range signal indicates that the signal present on the BCD outputs is not indicative of the analog signal present on input 210.

A voltage reference is required to be applied to the input 218 of analog-to-digital converter 18. The voltage reference signal must be very precise. One suitable form for providing the voltage reference signal is that of using a voltage reference 220 whose input is connected to a voltage source, for example, 5 volts. The output of voltage reference source 220 is connected via a resistor 222 to input 218 and also to electrical ground. The value of resistor 222 sets the voltage level present on line 218. One example voltage level is that of 0.2 volts.

The sample rate of the analog-to-digital converter 18 is set by a capacitor 224 and a resistor 226. Analog-to-digital converter 18 has a fixed sample rate set by capacitor 224 and resistor 216 and, thus, provides a BCD output signal to data bus 216 after each sample time period has lapsed. A representative sample time is that of one sixth of a second.

Capacitors 226 and 228 are for purposes of stabilization and are well-known in the art.

The digital signal, in BCD format, is provided by an eight bit parallel bus 216 to the port A input of a parallel interface adapter 230. In addition, the CA1 signal on line 212 and the CA2 signal on line 214 are also applied as inputs to parallel interface adapter 230.

Parallel interface adapter 230 is a slave of the microprocessor, designated generally by reference numeral 232. The parallel interface adapter 230 provides the BCD signal from port A to the microprocessor data bus 234 on command from the microprocessor 232. Similarly, parallel interface adapter 230 on command from microprocessor 232 provides the output signal on microprocessor bus 234 to the utilization device 22.

Parallel interface adapter 230 can take any suitable form. One suitable type, for example, is that of the MC6821 manufactured by the Motorola Corporation. Other suitable forms for the parallel interface adapter 230 are contemplated by the present invention.

Microprocessor 232 controls the operation of the parallel interface adapter 230 in the following fashion. Microprocessor 232 first polls the status register associated with CA1 and CA2 signals. This status register has a hexidecimal address, for example, of 0080, as shown in the system memory map of FIG. 4, discussed below. This polling of the status register containing the CA1 and CA2 signals is performed by microprocessor 232 by providing a read signal on a line 236, a selected register address signal on lines 238 and 240, an enabled (E) signal on a line 242, and a valid memory address (VMA) signal on a line 244. In addition, the A7 address signal on line 246 applied to the chip select 1 (CS1) input of parallel interface adapter 230 must be in the high state, while the A15 address signal on a line 248 applied to the chip select 2 ($\overline{CS2}$) must also be in the low state.

This addressing scheme for the parallel interface adapter 230 eliminates the need for providing the entire 16 line address to parallel interface adapter 230 from microprocessor 232. In other words, the presence of an address signal on line 246, corresponding to the A7 address output, indicates that the microprocessor is operating in the system memory map above its random access memory (RAM), as shown by the system memory map of FIG. 4. In addition, the actions of an address signal on the A15 line 248 indicates that the microprocessor is operating below the read only memory (ROM) region of the system memory map, as shown by FIG. 4.

When the microprocessor 232 has provided the read signal on line 236, the enable signal on line 242, the valid memory address signal on line 244, and the proper address signals on lines 246 and 248, as well as the register select on lines 238 and 240, the parallel interface adapter 230 provides on the microprocessor data bus 234 the contents of its status register at hexidecimal address 0080, which contains the CA1 and CA2 signals. When this address signal is obtained, the parallel interface adapter 230 provides a signal on the microprocessor data bus 234 indicative of whether a sample is ready to be provided on the microprocessor data bus 234 from the port A input. It should be noted that the parallel interface adapter 230 for purposes of economy does not contain storage registers or latches for the sample signals provided on port A. Thus, the microprocessor must obtain the digital signals from the date bus 216 as they are provided by the analog-to-digital converter 18. This polling of the status registers provides the indication to the microprocessor 232 that it must be ready to cause the parallel interface adapter 232 to provide the signal at port A to data bus 234.

If the microprocessor obtains polling information indicating that a signal is about to be provided on port A by the analog-to-digital converter 18, microprocessor 232 can then cause this signal to be provided by the parallel interface adapter to the microprocessor data bus 234. Thereafter, the microprocessor 232 can accept this BCD digital signal for processing at its data input port.

By this point in the explanation, it has become apparent that the analog-to-digital converter 18 is operating asynchronously with respect to the microprocessor system made up of microprocessor 232, parallel interface adapter 230 and read only memory (ROM) 250. This asynchronous operation means that the digital samples provided by the analog-to-digital converter at the sample rates set by capacitor 224 and resistor 226 are not provided on command of the microprocessor 232. However, the microprocessor 232 makes the decision when to accept these digital signals present at its port A of the parallel interface adapter 230.

The program which controls the operation of the microprocessor 232 is stored in the read only memory (ROM) 250. ROM 250 can take any suitable form. In most systems contemplated by the device and method of the present invention, ROM 250 would only have to have a one kilobyte or two kilobyte capacity. In the one kilobyte case, a representative example for ROM 250 is that of the 2758 made by the Intel Corporation of the United States. In the case of the 2 kilobyte ROM 250, a representative example is the 2716 manufactured by the Intel Corporation.

Microprocessor 232 reads the program information out of ROM 250 on microprocessor data bus 234 by providing ROM 250 with appropriate address and control signals. These appropriate control signals consist of (1) an appropriate address signal on an address bus 252 which designates the storage location in ROM 250 at which the information to be read out is located, (2) an inverted enable signal on a line 254, and (3) an enable signal $\overline{CE}$ on a line 256 which is present only when the microprocessor 232 is operating in the upper portion of the system memory map. The use of the signals on lines 254 and 256 eliminate the need for a 16 line address bus 252 to be provided between microprocessor 232 and ROM 250. In other words, the signal on line 256 is absent only when the signal on line A15 is in the high state (indicating that the microprocessor 232 is operating above the F300 hexidecimal address, as shown in FIG. 4) and that a valid memory address signal is present on line 244. The $\overline{CE}$ signal on line 256 is provided at the output of a NAND gate 258 whose inputs are connected respectively to the A15 address of microprocessor 232 and the valid memory address line 244.

The inverted enable signal on line 254 is provided by an inverter 260 of conventional design connected to the enable line 242. The inversion of the enable signal on line 254 is only to accommodate ROM 250. Obviously, the non-inverted enable signal could also be used as another one of the control signals.

ROM 250 provides on the microprocessor data bus 234 the information stored at the location addressed by microprocessor 232 using the control signal scheme discussed above. Thus, ROM 250 only can be read out by microprocessor 232. ROM 250 can be programmed using any number of presently available methods, such as mask or electronic programming.

Microprocessor 232, after performing the processing on the digital signals provided from the analog-to-digital converter 18 through port A of the parallel interface data bus 234. This output signal, in turn, is provided at port B of parallel interface adapter 230 to the utilization device 22 when proper control signals are provided to the parallel interface adapter 230 by microprocessor 232. The control signals are similar to those used with respect to the addressing of port A: (1) a write signal on line 236, (2) an enable signal on line 242, (3) an A7 address signal on line 246, and (4) the absence of an A15 address signal on line 248. These control signals indicate the 0081 hexidecimal address of Port B peripherally, as shown by the system map of FIG. 4. It should be noted that the status registers for CB1 and CB2 associated with port B of parallel interface adapter 230 are not used in the present invention because port B is only being used as an output and not as an input port.

The output signal on port B is provided to a utilization device 22. Typically, the output signal on port B is in a BCD format. It should be understood, however, that the present invention contemplates other digital formats for the output signal.

One suitable form for the utilization device 22 is that of a visual display which displays numerically the value of the output signal. Such a visual display could include a digit driver stage 280, which indicates to a visual display unit 282 which combination of the four display elements (not shown) is to be lighted, and also would include a segment driver stage 284 which would cause the various segments of each of the displays to be scanned. Since the segments of each display element are scanned at a rate faster than the eye can detect, the eye acts as an integrator and thus the display appears to be on continuously to the observer. Such a scanned display technique is well-known in the art and thus is not discussed in detail herein.

As stated above, utilization device 22 can take any number of other suitable forms. For example, utilization device 22 could constitute a single output light or audible signal which indicates whether a given parameter or parameters of the organism is present or absent (not shown). Alternately, utilization device 22 could take the form of a telemetry unit or a storage unit (not shown).

Two representative programs which can be implemented by microprocessor 232 are shown by the flow charts of FIGS. 5 and 6.

Referring first to FIG. 5, the reset routine is shown in flow chart form. Before this routine is discussed, it should be noted that the microprocessor 232 is provided with a reset circuit made up of a momentary contact switch 290 connected between the reset input of microprocessor 232 and electrical ground. A capacitor 291 is connected between the reset input and electrical ground. A voltage source, for example, 5 volts, is connected via a resistor 292 to capacitor 291. When microprocessor 232 is first turned on, the capacitor is in the uncharged state, which causes the reset input to be in the low state. At this time, microprocessor 232 is automatically caused to be reset. Thereafter, microprocessor 232 can be reset by the momentary depression of switch 290, which causes capacitor 291 to be discharged so that the reset input goes to the low state. The reset input of microprocessor 232 is a Schmidt trigger and thus detects when the reset input goes to the high state.

Referring again to FIG. 5, the reset routine is initiated by either turning on microprocessor 232 or momentarily depressing switch 290. Either of these steps cause the start mode to occur, as indicated by block 500. Thereafter, microprocessor 232 initializes the parallel interface adapter 230, as indicated by block 502. This initialization of parallel interface adapter 230 takes the form of setting all of the shift registers and control registers of parallel interface adapter 230 to a desired state. Once these shift and control registers have been initialized, microprocessor 232 then reads the first digital signal sample of the analog input at input 210 of analog-to-digital converter 18, as indicated by block 504. The digital signal provided at port A is then supplied by microprocessor 232 to the utilization device 22, where display 282 provides the visual display of the actual potential level of the electromagnetic field present between the reference and test electrodes. The display of this digital signal is indicated by block 506. A do loop for this voltmeter function of the device of the present invention of FIG. 3 is indicated by line 508. This continuous reading of each sample provided by analog-to-digital converter 18 continues until the operator causes the microprocessor 232 to enter the run routine.

Microprocessor 232 enters the run routine when a nonmaskable interrupt signal is provided to the nonmaskable interrupt input of microprocessor 232. The nonmaskable interrupt signal is provided by momentarily depressing a switch 293, connected between the nonmaskable interrupt input and electrical ground. A voltage source, for example, 5 volts, is connected via a resistor 295 to the nonmaskable interrupt signal. Thus, when switch 292 is depressed, the signal present on the nonmaskable interrupt input goes to the low state, causing the microprocessor 232 to interrupt the reset routine and start the run routine.

Referring now to FIG. 6, the provision of the nonmaskable interrupt signal which initiates the run routine is indicated by block 600. Once the nonmaskable interrupt signal has been provided, microprocessor 232 initializes all timers and registers in the system, as indicated by block 602. Thereafter, microprocessor 232 reads the first digital signal sample present on port A from analog-to-digital converter 18, as indicated by block 604. This digital signal is then normalized by dividing it by the total number of samples of the test. For example, when the period of the test is 30 seconds and a sampling rate of one-sixth of a second is being used, the normalization would be provided by dividing each of the digital signal samples by a denominator of 180. This normalization is indicated by block 606. The normalized value is then summed with the previous data values, as indicated by block 608. Thus, a running sum of the normalized values is obtained as the microprocessor executes the program contained in ROM 250 during the course of the run routine. The microprocessor then determines whether the full number of test samples have been obtained. For example, if 180 test samples have not been obtained, the test is still ongoing and the run routine is continued. This testing of whether the number of test samples has been obtained is indicated by the IF block 610.

In the event that the total number of samples have not been obtained, a do loop 612 causes the run routine to go back to reading an additional sample, as indicated by block 604. Thereafter, the routine is continued through block 604 to block 608 and another decision is made by the IF block 610 to decide whether the total number of samples have been obtained.

Once the total number of samples have been obtained, the sum indicated by block 608 constitutes the total sum of all of the samples during the period of the test. Thereafter, microprocessor 232 causes this sum to be displayed by the utilization device 282, as indicated by block 612.

It is apparent to those skilled in the art that other processing routines could be utilized in accordance with the device and method of the present invention so as to provide an output signal indicative of one or more parameters of the living organism as indicated by the state of the electromagnetic field. The reset and run routines shown in FIGS. 5 and 6, respectively, are thus representative and are not limiting to the routines which can be performed in accordance with the device and method of present invention.

FIG. 4 shows the system memory map of the system shown in FIG. 3. As shown, the random access memory (RAM) is contained between the hexidecimal address 0000 and 007F. The register selects in the parallel interface adapter 230 are contained between hexidecimal addresses 0080 and 0083. The portion of the memory map between hexidecimal addresses 0084 and F2FF, which constitutes an approximate 61 kilobyte address space, is unused in the present system. The hexidecimal addresses above F300 are used for addressing ROM 250.

As is apparent, the 16 bit address is used in the system shown in FIG. 3. Thus, 64 kilobytes of addresses are available. It should be understood that any address scheme could be used by the device and method of the present invention, including an 8 bit or 12 bit address scheme.

EXAMPLE 1

The device and method of the present invention has been used experimentally to assess the time of ovulation of human subjects. Eight test subjects were used. A total of sixteen cycles were assessed. The potential level between the index fingers, middle fingers, and thumbs was measured and these values were averaged for each daily test. The electrodes described with respect to FIG. 2 were used and these electrodes included an insulated housing. Ovulation was indicated by a peak aggregate value of the potential level of the electromagnetic field within plus or minus two days of ovulation. These ovulation peaks were compared against the time of ovulation as indicated by basal body temperature shifts and in some cases change in cervical mucus viscosity. In that basal body temperature is presently considered one of the most accurate method of assessing the time of ovulation, the test results were compared against the basal body temperature results. A correlation of 87.5% was obtained. Additional tests in this area are now being planned.

This should be compared to the very inaccurate results obtained by other researchers measuring the potential level of the electromagnetic field of the subjects using conventional devices. For example, reference is made to the results set out in: Poulson, A. Marsh, M.D. and Grant Carter, M.D., "Detection of Ovulation by a Method of Change in Finger-Finger Electropotential Readings," *Contraception*, Vol. 18, No. 3, September 1978, pages 295–308; Kuhtik, Nellie J., "An Abstract of an Experimental Investigation of Ovulation in White Females and Bioelectric Potential Differences," Ph.D. Thesis, New York University, 1968.

EXAMPLE 2

The device and method of the present invention is being used experimentally to assess the presence or absence of breast cancer. The reference electrode is disposed on the opposite nipple of the breast under test. Normally, four test points per breast are used, with a test point falling within each quadrant of the breast under test. The absence of cancer is indicated by a positive polarity of the electromagnetic field, while the presence of cancer is indicated by negative polarity of the electromagnetic field. Additional tests in this area are also ongoing.

EXAMPLE 3

The device and method of the present invention has been used experimentally to monitor the healing rate of a lesion of a human subject. The reference electrode was disposed on the hand not having the lesion, while the test electrode was disposed on the lesion. Tests were conducted every day. The potential level of the electromagnetic field assumed a substantially bell-shaped curve of positive polarity with respect to time. After healing had been completed, the potential level assumed a quiescent state.

While there have been shown and described what are at present considered to be the preferred embodiments of the present invention, modifications thereto will readily occur to those skilled in the art. It is not desired, therefore, that the invention be limited to the specific arrangements shown and described, and it is intended to cover in the appended claims all such modifications as fall within the true spirit and scope of the invention.

What is claimed is:

1. Apparatus for measuring the condition of a living organism as a function of the electrical potential of an electromagnetic field present in said living organism between a reference location and a test location of said living organism, said apparatus comprising:
    reference electrode means and test electrode means electrically contactable with the surface of a living organism at relatively spaced apart locations for detecting the electrical potential of the electromagnetic field of said organism between said test location and said reference location;
    analog-to-digital converter means coupled to said reference and test electrode means for generating a digital signal as a function of the electrical potential detected by said electrode means; and processing means coupled to said analog-to-digital converter means for generating an output signal as a function of said digital signal said processing means output signal being a measure of the condition of said living organism.

2. Apparatus according to claim 1, wherein said electromagnetic field comprises a varying DC voltage signal, and said apparatus further comprises filter means interposed between said reference and test electrode means and said analog-to-digital converter means for removing undesirable AC components superimposed on said varying DC signal prior to said DC voltage signal being operated on in said analog-to-digital converter means.

3. Apparatus according to claim 1 wherein at least one of said reference and test electrodes comprises:
an outer layer consisting essentially of concentrated NaCl electrically contactable with said living organism;
an adjacent inner layer consisting essentially of AgCl in electrical contact with said NaCl layer;
a next adjacent inner layer consisting essentially of Ag in electrical contact with said AgCl layer; and
an electrical lead electrically contacting said Ag layer.

4. Apparatus according to claim 1 wherein each of said reference and test electrodes comprises:
an outer layer consisting essentially of concentrated NaCl electrically contactable with said living organism;
an adjacent inner layer consisting essentially of AgCl in electrical contact with NaCl layer;
a next adjacent inner layer consisting essentially of Ag in electrical contact with said AgCl layer; and
an electrical lead electrically contacting said AG layer.

5. Apparatus according to claim 3 or 4, wherein said outer layer is composed of a polymer of NaCl.

6. Apparatus according to claim 3 or 4, wherein said outer layer is composed of a colloid of NaCl.

7. Apparatus according to claim 1, wherein at least one of said reference and test electrodes is composed of materials which substantially inhibit production of a battery effect between the electrode and the living organism with which said electrode is in electrical contact.

8. Apparatus according to claim 1, wherein each of said reference and test electrodes is composed of materials which substantially inhibit production of a battery effect between the electrode and the living organism with which said electrode is in electrical contact.

9. Apparatus according to claim 1, wherein said analog-to-digital converter means exhibits an effective input impedance of greater than 8 megohms and less than 1,000 megohms.

10. Apparatus according to claim 1, further comprising low pass filter means for filtering output signals from said electrode means and for supplying said filtered signals to said analog-to-digital converter means.

11. Apparatus according to claim 10, wherein said low pass filter means has a substantially 3 dB cutoff frequency of greater than or equal to about 100 hertz.

12. Apparatus according to claim 1, wherein said digital-to-analog converter includes means for sampling the potential levels detected by said electrode means and for generating a digital signal corresponding to each sampled level.

13. Apparatus according to claim 12, wherein said digital signal is in binary-coded-decimal format.

14. Apparatus according to claim 1, wherein said processing means comprises a programmed digital signal processing means having a stored program for providing said output signal as a function of said digital signal and said stored program.

15. Apparatus according to claim 1, wherein said digital-to-analog converter means includes means for sampling the potential levels detected by said electrode means and for generating a digital signal corresponding to each sampled level; and
wherein said processing means includes means for generating said processing means output signal as a statistical function of said digital signal.

16. Apparatus according to claim 15, wherein said sampling means samples said detected potential levels at a substantially constant rate.

17. Apparatus according to claim 1, wherein said processing means comprises central processor means, interface means, data bus means coupled to said interface means and said central processor means, and stored program means coupled to said data bus means for providing program instructions, including read and write instructions to said data bus in accordance with selected address and control signals:
(a) said central processor means sending and receiving digital data to and from said data bus in accordance with a read and write signal, respectively, and in accordance with address and control signals from said stored program means, and
(b) said interface means being responsive to said digital signal output of said converter means for providing said digital signal to said data bus in accordance with said read signal and selected address and control signals, and for providing said output signal from said data bus in accordance with said write signal and selected address and control signals.

18. Apparatus according to claim 17, wherein said central processor comprises a microprocessor and wherein said stored program means comprises a read only memory.

19. Apparatus according to claim 1, further comprising means for visually and/or audibly displaying said processing means output signal.

20. Apparatus according to claim 1, further comprising telemetry means for transmitting said processing means output signal.

21. Apparatus according to claim 1, further comprising means for storing said processing means output signal.

22. Apparatus according to claim 1, wherein the condition of said living organism being measured is the presence of atypical cellular formations.

23. Apparatus according to claim 1, wherein the condition of said living organism being measured is an indication of ovarian events therein.

24. Apparatus according to claim 1, wherein the condition of said living organism being measured is the level of neurological activity therein.

25. Apparatus according to claim 1, wherein the condition of said living organism being measured is the viability level of seeds.

26. Apparatus according to claim 1, wherein the condition of said living organism being measured is the state of consciousness thereof.

27. A method for measuring the condition of a living organism, comprising the steps of:
   detecting the electrical potential of an electromagnetic field present in said living organism between a reference location and a test location on said living organism;
   generating a digital signal as a function of the detected electrical potential of said electromagnetic field of said organism; and
   processing said digital signal and generating an output signal as a function of the processed digital signal, said output signal being a measure of the condition of said living organism.

28. The method according to claim 27, wherein the condition of said living organism being measured is the presence of atypical cellular formations.

29. The method according to claim 27, wherein the condition of said living organism being measured is an indication of ovarian events therein.

30. The method according to claim 27, wherein the condition of said living organism being measured is the level of neurological activity therein.

31. The method according to claim 27, wherein the condition of said living organism being measured is the viability level of the seeds.

32. The method according to claim 27, wherein the condition of said living organism being measured is the state of consciousness thereof.

33. A method according to claim 27, further comprising the step of low pass filtering an analog signal representing the detected electrical potential of the electromagnetic field of said organism between said reference location and said test location prior to converting said analog signal to a corresponding digital signal.

34. A method according to claim 27, wherein said step of generating a digital signal comprises the step of sampling the detected electrical potential at a predetermined sampling rate and providing a digital signal corresponding to each sampled level.

35. A method according to claim 34, further comprising generating said output signal as a function of said sampled digital signals.

36. A method according to claim 34, further comprising generating said output signal as a statistical function of said sampled digital signals.

37. A method according to claim 34, further comprising generating said output signal as a function of said sampled digital signals and a stored program.

38. A method according to claim 27 in which said electrical potential is measured by reference electrode means and test electrode means electrically contactable with the surface of the living organism at relatively spaced apart reference and test locations, respectively, said method comprising the further step of:
   substantially inhibiting production of a battery effect between at least one of said reference and test electrodes and the living organism with which said at least one electrode is in electrical contact.

39. A method according to claim 27 in which said electrical potential is measured by reference electrode means and test electrode means electrically contactable with the surface of the living organism at relatively spaced apart reference and test locations, respectively, said method comprising the further step of:
   substantially inhibiting production of a battery effect between said reference and test electrodes and the living organism with which said electrodes are in electrical contact.

* * * * *